United States Patent
Sharkey et al.

(10) Patent No.: US 6,757,565 B2
(45) Date of Patent: Jun. 29, 2004

(54) ELECTROSURGICAL INSTRUMENT HAVING A PREDETERMINED HEAT PROFILE

(75) Inventors: Hugh R. Sharkey, Redwood City, CA (US); John E. Ashley, San Francisco, CA (US); Kobi Iki, San Carlos, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 10/071,470

(22) Filed: Feb. 8, 2002

(65) Prior Publication Data

US 2003/0153906 A1 Aug. 14, 2003

(51) Int. Cl.[7] .............................. A61F 7/12; A61F 2/00
(52) U.S. Cl. .................... 607/99; 607/101; 607/102
(58) Field of Search .................... 606/41, 42, 49, 606/50; 607/96, 98–99, 101–102, 115–116

(56) References Cited

U.S. PATENT DOCUMENTS

| | | |
|---|---|---|
| 2,050,904 A | 8/1936 | Trice |
| 3,460,539 A | 8/1969 | Anhalt |
| 3,828,780 A | 8/1974 | Morrison, Jr. |
| 4,202,337 A | 5/1980 | Hren et al. |
| 4,326,529 A | 4/1982 | Doss et al. |
| 4,375,220 A | 3/1983 | Matuias |
| 4,381,007 A | 4/1983 | Doss et al. |
| 4,397,314 A | 8/1983 | Vaguine |
| 4,483,338 A | 11/1984 | Bloom et al. |
| 4,517,975 A | 5/1985 | Garito et al. |
| 4,593,691 A | 6/1986 | Lindstrom et al. |
| 4,601,705 A | 7/1986 | McCoy |
| 4,686,986 A | 8/1987 | Fenyö et al. |
| 4,765,331 A | 8/1988 | Petruzzi et al. |
| 4,815,462 A | 3/1989 | Clark |

(List continued on next page.)

FOREIGN PATENT DOCUMENTS

| | | |
|---|---|---|
| EP | 0 479 482 | 4/1992 |
| EP | 0 729 730 | 4/1996 |
| WO | WO 92/02272 | 2/1992 |
| WO | WO 92/10142 | 6/1992 |
| WO | WO 93/01774 | 7/1992 |
| WO | WO 93/15664 | 8/1993 |
| WO | WO 95/10981 | 4/1995 |
| WO | WO 95/18575 | 7/1995 |
| WO | WO 95/30373 | 11/1995 |
| WO | WO 96/32051 | 10/1996 |
| WO | WO 96/39914 | 12/1996 |
| WO | WO 98/07468 | 2/1998 |
| WO | 98/11944 | 3/1998 |
| WO | WO 98/17190 | 4/1998 |
| WO | WO 98/34558 | 8/1998 |
| WO | WO 99/47058 | 9/1999 |
| WO | WO 01/49196 | 7/2001 |

*Primary Examiner*—Roy D. Gibson
(74) *Attorney, Agent, or Firm*—Fish & Richardson P.C.

(57) ABSTRACT

An electrosurgical instrument is provided, having a holding formation, an elongated probe, an electrode, and a conductor. The elongated probe is connected to and extends from the holding formation. The electrode is located on an end of the elongated probe opposing the holding formation, and has a leading edge and a face. The electrode is locatable so that the face is substantially in a horizontal plane and the leading edge is above the horizontal plane. The conductor extends along the elongated probe and has a portion connected to the electrode to provide RF power thereto. The electrode creates a temperature profile with a temperature adjacent to the leading edge being higher than a temperature adjacent to the face.

39 Claims, 4 Drawing Sheets

U.S. PATENT DOCUMENTS

| | | | |
|---|---|---|---|
| 4,823,791 A | | 4/1989 | D'Amelio et al. |
| 4,907,589 A | | 3/1990 | Cosman |
| 4,944,727 A | | 7/1990 | McCoy |
| 4,976,709 A | | 12/1990 | Sand |
| 5,009,656 A | * | 4/1991 | Reimels ..................... 606/48 |
| 5,085,659 A | | 2/1992 | Rydell |
| 5,103,804 A | | 4/1992 | Abele et al. |
| 5,191,883 A | | 3/1993 | Lennox et al. |
| 5,213,097 A | | 5/1993 | Zeindler |
| 5,230,334 A | | 7/1993 | Klopotek |
| 5,261,906 A | | 11/1993 | Pennino et al. |
| 5,304,169 A | | 4/1994 | Sand |
| 5,323,778 A | | 6/1994 | Kandarpa et al. |
| 5,334,193 A | | 8/1994 | Nardella |
| 5,348,554 A | | 9/1994 | Imran et al. |
| 5,364,395 A | | 11/1994 | West, Jr. |
| 5,366,443 A | | 11/1994 | Eggers et al. |
| 5,395,363 A | | 3/1995 | Billings et al. |
| 5,433,739 A | | 7/1995 | Sluijter et al. |
| 5,451,224 A | | 9/1995 | Goble et al. |
| 5,458,596 A | | 10/1995 | Lax et al. |
| 5,480,397 A | | 1/1996 | Eggers et al. |
| 5,480,398 A | | 1/1996 | Eggers et al. |
| 5,484,432 A | | 1/1996 | Sand |
| 5,527,331 A | | 6/1996 | Kresch et al. |
| 5,569,242 A | | 10/1996 | Lax et al. |
| 5,593,406 A | | 1/1997 | Eggers et al. |
| 5,683,366 A | | 11/1997 | Eggers et al. |
| 5,697,281 A | | 12/1997 | Eggers et al. |
| 5,697,536 A | | 12/1997 | Eggers et al. |
| 5,697,882 A | | 12/1997 | Eggers et al. |
| 5,697,909 A | | 12/1997 | Eggers et al. |
| 5,700,262 A | | 12/1997 | Acosta et al. |
| 5,718,701 A | | 2/1998 | Shai et al. |
| 5,766,153 A | | 6/1998 | Eggers et al. |
| 5,810,764 A | | 9/1998 | Eggers et al. |
| 5,810,809 A | | 9/1998 | Rydell |
| 5,904,709 A | | 5/1999 | Arndt et al. |
| 5,980,504 A | | 11/1999 | Sharkey et al. |
| 6,007,570 A | | 12/1999 | Sharkey et al. |
| 6,056,746 A | * | 5/2000 | Goble et al. .................. 606/48 |
| 6,068,628 A | | 5/2000 | Fanton et al. |
| 6,073,051 A | | 6/2000 | Sharkey et al. |
| 6,095,149 A | | 8/2000 | Sharkey et al. |
| 6,099,514 A | | 8/2000 | Sharkey et al. |
| 6,109,268 A | | 8/2000 | Thapliyal et al. |
| 6,122,549 A | | 9/2000 | Sharkey el al. |
| 6,126,682 A | | 10/2000 | Sharkey et al. |
| 6,135,999 A | | 10/2000 | Fanton et al. |
| 6,149,620 A | | 11/2000 | Baker et al. |
| 6,168,593 B1 | * | 1/2001 | Sharkey et al. ............... 606/34 |
| 6,190,381 B1 | | 2/2001 | Olsen et al. |
| 6,238,391 B1 | | 5/2001 | Olsen et al. |
| 6,254,600 B1 | | 7/2001 | Willink et al. |
| 6,258,086 B1 | | 7/2001 | Ashley et al. |
| 6,261,311 B1 | | 7/2001 | Sharkey et al. |
| 6,264,650 B1 | | 7/2001 | Hovda et al. |
| 6,270,476 B1 | | 8/2001 | Santoianni et al. |
| 6,277,112 B1 | | 8/2001 | Underwood et al. |
| 6,283,960 B1 | | 9/2001 | Ashley |
| 6,290,715 B1 | | 9/2001 | Sharkey et al. |
| 6,355,032 B1 | | 3/2002 | Hovda et al. |
| 6,379,350 B1 | | 4/2002 | Sharkey et al. |
| 6,416,508 B1 | | 7/2002 | Eggers et al. |
| 6,432,105 B1 | * | 8/2002 | Ellman et al. ................ 606/48 |
| 2001/0031963 A1 | | 10/2001 | Sharkey et al. |
| 2001/0056278 A1 | | 12/2001 | Neild et al. |
| 2002/0022830 A1 | | 2/2002 | Sharkey et al. |
| 2002/0065541 A1 | | 5/2002 | Fredricks et al. |
| 2002/0120259 A1 | | 8/2002 | Lettice et al. |

* cited by examiner

ELECTROSURGICAL INSTRUMENT HAVING A PREDETERMINED HEAT PROFILE

BACKGROUND OF THE INVENTION

1). Field of the Invention

This invention relates to an electrosurgical instrument of the kind used for electrosurgical arthroscopy.

2). Discussion of Related Art

Arthroscopic surgery is often used to treat degenerating cartilage. Cartilage on the back of the patella, for example, tends to wear down due to overuse into collagen fibrils having bases attached to remaining viable cartilage. The fibrils themselves then tend to cause acceleration in the degeneration process of the viable cartilage, and the "wear" debris from the fibrils irritates the joint lining. This irritation can be a source of pain as the fibrils break down and break off as debris which may necessitate joint replacement.

There are several interventions a surgeon may choose when addressing these lesions of the articular cartilage. While some surgeons feel the lavaging (irrigating) the joint is sufficient, many more surgeons endeavor to remove the excess material in an attempt to decrease the "wear" debris that originates from these strands of cartilage. One common way of addressing these lesions is with the use of mechanical shavers as are commonly used in arthroscopic surgery to "shave" off the long fronds of cartilage. This procedure is called a chondroplasty.

In another arthroscopic treatment method, a surgeon inserts an electrosurgical probe through an incision or opening formed in a body of a patient. Radio frequency (RF) power is then provided to an electrode at the end of the probe, which creates ohmic heating of an area surrounding the electrode. The fibrils are denatured by the heat when the electrode is brought into contact with the fibrils, which causes the fibrils to congeal together, forming an intact surface.

In order to effectively denature the fibrils, it is required that the fibrils be exposed to a relatively high temperature, for example, 70° C. or greater. Such high temperature not only denatures the fibrils, but has the potential to cause permanent damage to the viable cartilage to which the fibrils are attached. The high temperature causes chondrocyte death because the cartilage does not regenerate. The typical high temperature profiles of non-thermally controlled prior art probes may also deliver too much thermal energy which may also cause avascular necrosis (AVN) of the underlying bone structure, requiring total joint replacement.

Thus, what is needed is a surgical probe which can effectively address the fibrils while protecting viable cartilage. The probe should be able to deliver a controlled amount of energy for thermal treatment with a variable temperature profile to treat the different tissues at the surgical site.

BRIEF SUMMARY OF THE INVENTION

According to one aspect of the invention, an electrosurgical instrument is provided, having a holding formation, an elongated probe, at least one electrode, and a conductor. The elongated probe is connected to and extends from the holding formation. The at least one electrode is located on an end of the elongated probe opposing the holding formation, and forms at least part of an electrode structure that has a leading edge and a face. The at least one electrode is locatable so that the face is substantially in a horizontal plane and the leading edge is above the horizontal plane. The conductor extends along the elongated probe and has a portion connected to the at least one electrode to provide RF power thereto. The at least one electrode creates a temperature profile with a temperature adjacent to the leading edge being higher than a temperature adjacent to the face.

The leading edge and the face are preferably on a single electrode.

The leading edge may have a smaller radius of curvature than the face. The face may be substantially flat. The leading edge may be substantially sharp. The leading edge may point in a direction away from the horizontal plane.

There is preferably no material of the electrode directly below the leading edge in the horizontal plane.

The electrode may have a convex cam surface between the leading edge and the face. The convex cam surface may extend up to the leading edge.

The at least one electrode may have a trailing edge on a side of the face opposing the leading edge. The trailing edge may be at substantially the same distance from the horizontal plane as the leading edge.

The electrode may have an electrode opening therein. The electrode opening may have a diameter which is less than 50% of a diameter of the electrode measured in the same plane. The electrode opening may extend through the face. The electrosurgical instrument may further include a thermally conductive plug in the opening at or near the face, and a thermocouple in contact with the thermally conductive plug. The thermally conductive plug, at or near the face, is preferably made of an electrically insulating material.

Preferably, a line at right angles to the horizontal plane is at an angle with respect to an axis of the elongated probe. The angle may, for example, be at least 30°.

A lower surface of the elongated probe may be above the horizontal plane.

The holding formation may, for example, be a handle.

A method is provided for treating degenerative collagen fibrils, having bases attached to viable cartilage. A surface of an electrode structure is located adjacent to viable cartilage. A temperature profile is generated having a low temperature adjacent to the face and a high temperature at a location further from the viable cartilage than the face. The electrode structure is moved in a direction substantially parallel to a plane of the viable cartilage. Such movement first exposes each fibril to the location of the temperature profile having the high temperature, whereafter the surface moves over the fibrils.

Preferably, the location on the temperature profile having the higher temperature passes through an imaginary plane normal to the plane of the viable cartilage before the face passes through the imaginary plane.

BRIEF DESCRIPTION OF THE DRAWINGS

The invention is described by way of examples with reference to the accompanying drawings, wherein.

DETAILED DESCRIPTION OF THE INVENTION

Figure 1:
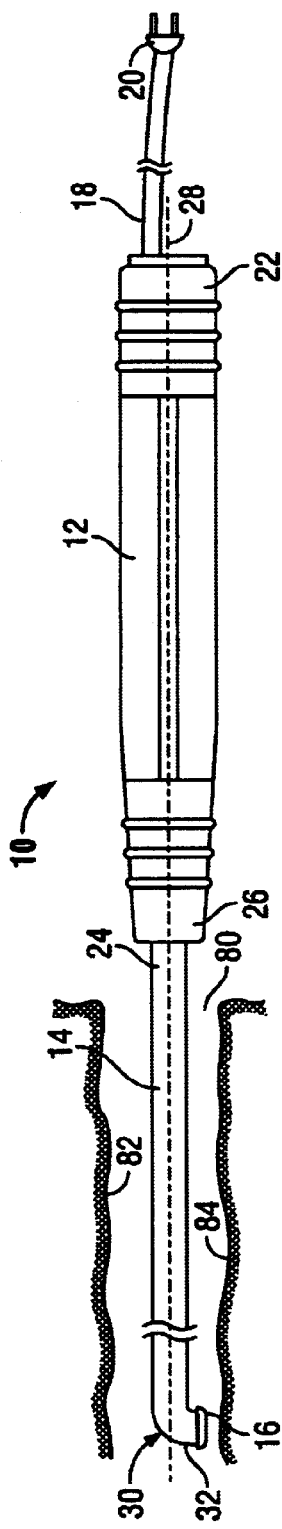
FIG. 1 is a cross-sectional side view illustrating an electrosurgical instrument according to an embodiment of the invention.

FIG. 1 of the accompanying drawings illustrates an electrosurgical instrument 10, according to an embodiment of the invention, including a handle 12, a composite elongated probe 14, an electrode 16, an electric cable 18, and an electric connector 20.

The electric connector 20 is connected one end of the electric cable 18 and an opposing end of the electric cable 18 is secured to a rear end 22 of the handle 12. A proximal end 24 of the composite elongated probe 14 is secured to a front end 26 of the handle 12 opposing the rear end 22. A common horizontal axis 28 extends through the handle 12 and the composite elongated probe 14. In this embodiment, a bend 30 is formed in the composite elongated probe 14 just short of a distal end 32 thereof and the electrode 16 is secured to the distal end 32. Another embodiment may have no bend at the distal end.

Figure 2:
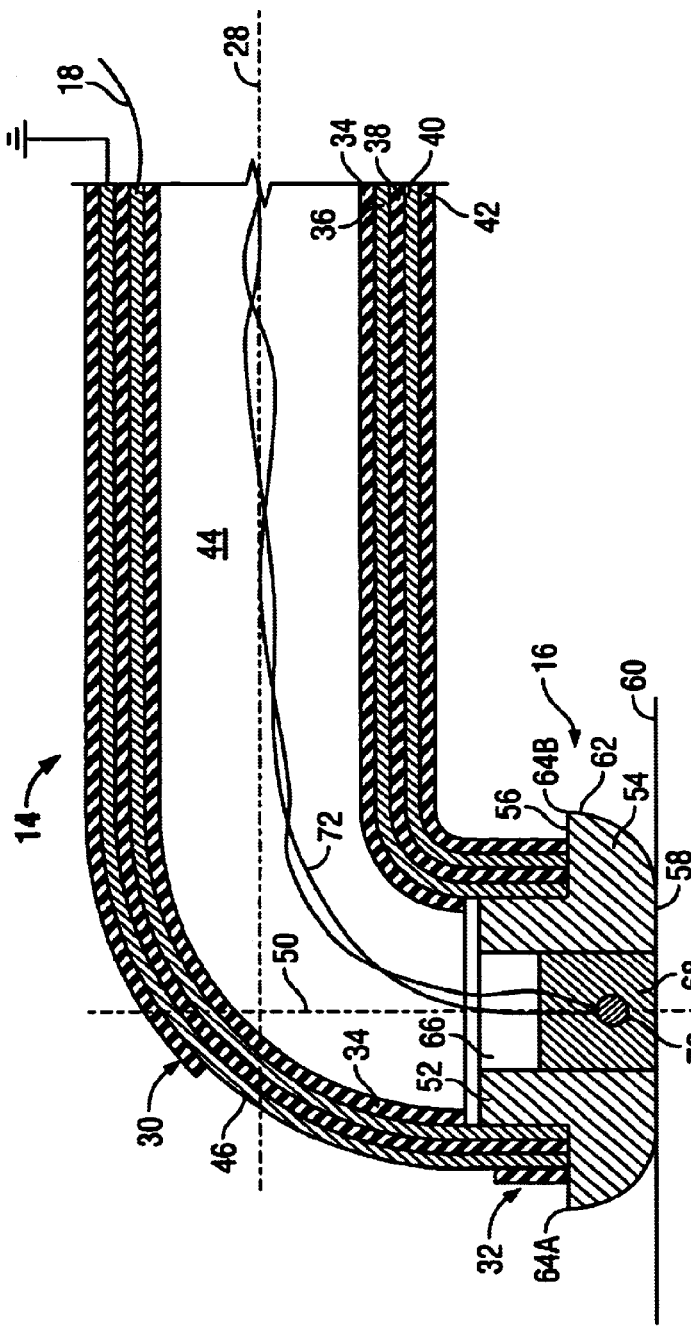
FIG. 2 is a cross-sectional side view of a distal end of a composite elongated probe of the electrosurgical instrument, and an electrode attached to the distal end.

Referring now also to FIG. 2, the composite elongated probe 14 includes a plurality of concentric coatings and tubes, including an inner insulator 34, a metal power conductor 36, and intermediate insulator 38, a metal ground conductor 40, and an outer insulator 42. The inner insulator 34 defines a passage 44 extending therethrough. The power conductor 36 is located around the inner insulator 34, and is insulated from the passage 44 by the inner insulator 34. The intermediate insulator 38 is located around the power conductor 36. The ground conductor 40 is located around the intermediate insulator 38, and is insulated from the power conductor 36 by the intermediate insulator 38. The outer insulator 42 surrounds the ground conductor 40 and provides an insulated outer surface for the composite elongated probe 14. Only a portion 46 of the ground conductor 40 near the distal end 32 is exposed on an external surface of the composite elongated probe 14. The electric cable 18 is attached to the power conductor 36 near its proximal end 24. The conductive metal may be a biocompatible metal such as nickel, stainless steel, platinum, tungsten, or their alloys, with tungsten being preferred.

The electrode 16 is made of an electrically conductive metal. Although shown in cross-section, it should be understood that, in this embodiment, the electrode 16 has circular dimensions which are symmetrically formed about a vertical axis 50. The circular dimensions allow for multidirectional use and a uniform temperature profile around the electrode 16. The geometry of the electrode 16 may be different in another embodiment, depending on application.

The electrode 16 has an upper portion 52 having a diameter of approximately 3 mm, and a lower portion 54 having a diameter of approximately 5 mm. In another embodiment, the diameter may be between 5 and 8 mm. A horizontal step 56 is formed where the electrode 16 transitions from the smaller diameter of the upper portion 52 to the larger diameter of the lower portion 54.

The lower portion 54 has a lower face 58. The electrode is depicted with the face 58 in a horizontal plane 60. The lower portion 54 also has a convex cam surface 62 connecting the face 58 with the step 56. A tip 64 is formed where the step 56 and the cam surface 62 meet. A leading edge 64A of the tip is located on the left of the face 58 at a distance of approximately 1.3 mm above the horizontal plane 60. In another embodiment, the leading edge 64A may be between 1 mm and 2 mm above the horizontal plane 60. A trailing edge 64B of the tip is located on the right of the face 58 at the same height from the horizontal plane 60 as the leading edge 64A. The leading edge 64A points upward and to the left, and the trailing edge 64B points upward and to the right. There is no material of the electrode 16 directly below either the leading or trailing edges 64A or 64B in the horizontal plane 60.

An inner surface of the power conductor 36 is exposed because the inner insulator 34 is not located in the distal end 32. The upper portion 52 is inserted into and contacts the inner surface of the power conductor 36. Electric current can flow from the electric cable 18 through the power conductor 36 to the electrode 16.

An electrode opening 66 is formed in the direction of the vertical axis 50 through the electrode 16. The electrode passage 66 extends into the lower face 58 through the electrode 16 out of the upper portion 52. A plug 68 of a thermally conductive but electrically insulating solder material is inserted into the electrode passage 66. A lower surface of the plug 68 is located in a plane of the lower face 58. A thermocouple 70 is located in the plug 68. Thermocouple wires 72 are connected to the thermocouple 70 and extend through the passage 44 to the handle 12 for temperature feedback.

Prior to use of the electrosurgical instrument 10, an incision or surgical portal 80 is made in a body of a patient. For purposes of consistency, it is assumed that the surgical portal 80 extends horizontally, and that it has upper and lower horizontal walls 82 and 84, respectively. A surgeon, holding the handle 12, inserts the electrode 16 horizontally into the surgical portal 80, followed by a portion of the composite elongated probe 14. Due to the angle of the axis 50 relative to the axis 28, and because the lower face 58 is lower than a lower surface of the composite elongated probe 14, the surgeon can position the lower face 58 adjacent to the viable cartilage of the lower wall 84.

The connector 20 is connected to an RF source (not shown). An RF source generates a voltage which is provided from the RF source through the connector 20, the cable 18, and through the power conductor 36 to the electrode 16. The surgical portal 80 is filled with an electrically conductive fluid, so that the lower portion 54 of the electrode 16 is electrically connected through the fluid to the portion 46 of the ground conductor 40 which is exposed. A proximal portion of the ground conductor 40 is connected to ground. A closed circuit is thereby provided, whereby RF current conducts through the electrode 16. The RF current heats the electrode 16, and the heat then radiates from the electrode 16 to tissue of an area surrounding the electrode 16.

Figure 3:
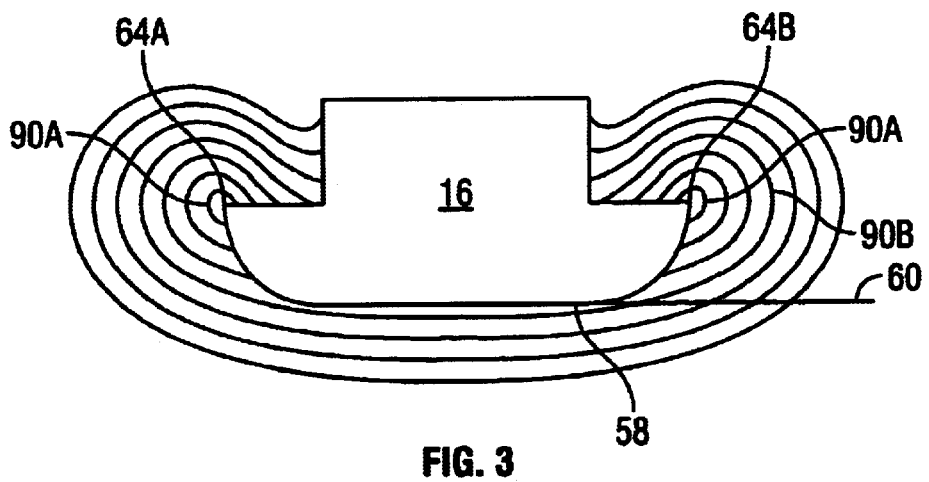
FIG. 3 is a cross-sectional side view illustrating isotherms generated by the electrode.
Figure 4:
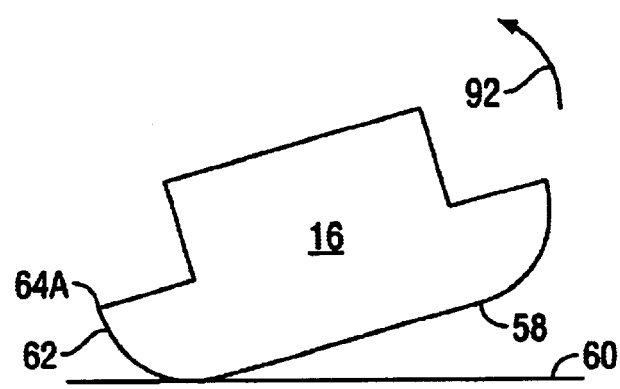
FIG. 4 is a cross-sectional side view illustrating pivoting of the electrode.

FIG. 3 illustrates a temperature profile around the electrode 16. The temperature profile is illustrated with isotherms 90. One isotherm 90A, in cross-section, has center points near the leading and trailing edges 64A and 64B. The isotherm 90A has a relatively high temperature of, for example, approximately 110° C. Another isotherm 90B located adjacent to the lower face 58 has a relatively low temperature of, for example, 55° C. The relatively high temperature at the leading and trailing edges 64A and 64B can be ascribed to the relatively small radii of the leading and trailing edges 64A and 64B, and particularly to the fact that they are relatively sharp. A higher current density is created near small radii than near large radii of the electrode 16, which creates the higher temperature near the small radii. The relatively low temperature adjacent to the lower face 58 can be ascribed to the fact that the lower face 58 is flat, and therefore has a radius of curvature (infinite), which is much larger than the radii of the leading and trailing edges 64A and 64B. What should be noted is that a relatively high temperature is created near the leading and trailing edges 64A and 64B distant from the horizontal plane 60 in which the lower face 58 is located. Even if the surgeon pivots the electrode 16 in a direction 92, as illustrated in FIG. 4, the cam surface 62 assists in keeping the leading edge 64A elevated from the horizontal plane 60.

Reference is again made to FIG. 2. Because the plug 68 is not electrically conductive, no heat is generated in the plug 68, which assists in creating a more accurate and even temperature profile across the lower face 58. The plug 68 has a diameter which is preferably at least 30% of the diameter of the lower face 58 to create a more even temperature profile, but preferably less than 50% of the diameter of the electrode 16, so that the electrode 16 still has sufficient thermal mass. The plug 68 is, however, still sufficiently thermally conductive so that heat will be conducted from the electrode 16 through the plug 68 to the thermocouple 70, which then provides temperature feedback through the thermocouple wires 72 to the RF source.

Figure 5:
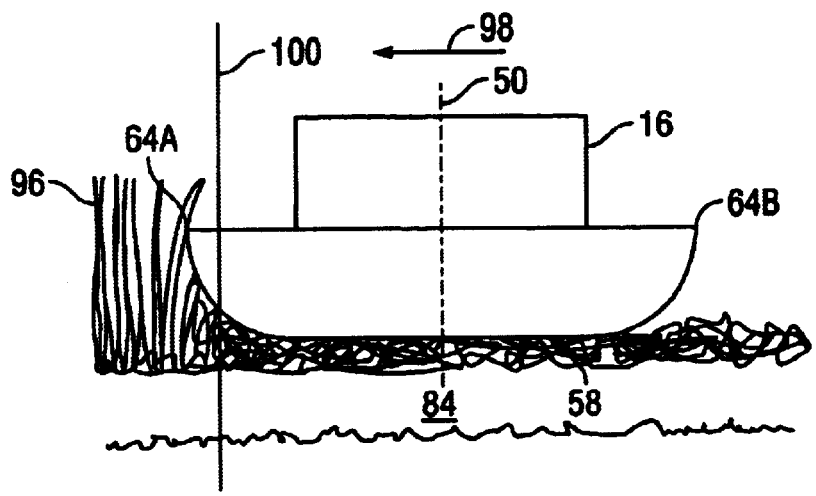
FIG. 5 is a side view illustrating how the electrode is used to treat degenerative collagen fibrils attached to viable cartilage.

FIG. 5 illustrates how the electrode 16 is used for treating degenerative collagen fibrils 96 attached to cartilage of the lower wall 84. The lower wall 84 consists of viable cartilage, for example, on the rear of the patella (not shown) or other cartilagenous surfaces. The fibrils 96 have bases attached to the viable cartilage of the lower wall 84. The relatively low temperature adjacent to the lower face 58 then causes no or minimal damage to the viable cartilage. The surgeon progresses the electrode 16 in a direction 98 substantially parallel to a plane of, and in contact with, the lower wall 84. Each fibril 96 is first exposed to the relatively high temperature adjacent to the leading edge 64A, which partially denatures the fibril 96. Further movement of the electrode 16 in the direction 98 moves the lower face 58 over the partially denatured fibrils 96. The lower temperature adjacent to the lower face 58 causes less denaturization of the fibrils 96, but is still sufficiently high to continue to coagulate the partially denatured fibrils 96 when the lower face 58 moves over the partially denatured fibrils 96. What should be noted is that the leading edge 64A passes through an imaginary vertical plane 100 before the lower face 58 passes through the imaginary vertical plane, so that the fibrils 96 are first partially denatured by the relatively high temperature adjacent to the leading edge 64A before congelation by the lower face 58.

It can thus be seen that the degenerative fibrils 96 are treated with only a minimum amount of damage to the viable cartilage in the lower wall 84 because of the relative lower temperature. Fibrils to the right of the electrode 16 may be treated in a similar manner by moving the electrode 16 in a direction opposite to the direction 98. As mentioned, the electrode 16 is symmetrical about the vertical axis 50, so that the electrode 16 can also be moved through fibrils in a direction at right angles to the direction 98 with similar results.

In the above-described embodiment, the electrosurgical instrument 10 is of a bipolar configuration. In a bipolar arrangement, current returns through a ground conductor such as the ground conductor 40, and the majority of the heat is generated within the electrode 16. In a monopolar arrangement, current does not return through a ground conductor. Instead, a conductive pad is located on a patient, and current returns through the patient and to the conductive pad. In a monopolar arrangement, the majority of the heat is not generated in the electrode, but in material adjacent to the electrode. It is believed that a monopolar arrangement will create a temperature profile which is similar to the temperature profile illustrated in FIG. 3.

Figure 6:
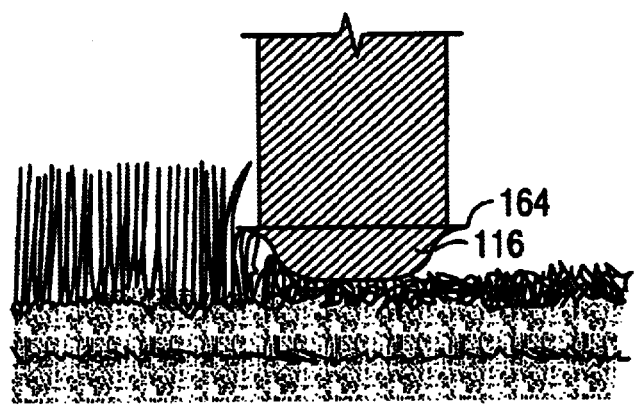
FIG. 6 is a side view illustrating one alternative embodiment of an electrode.
Figure 7:
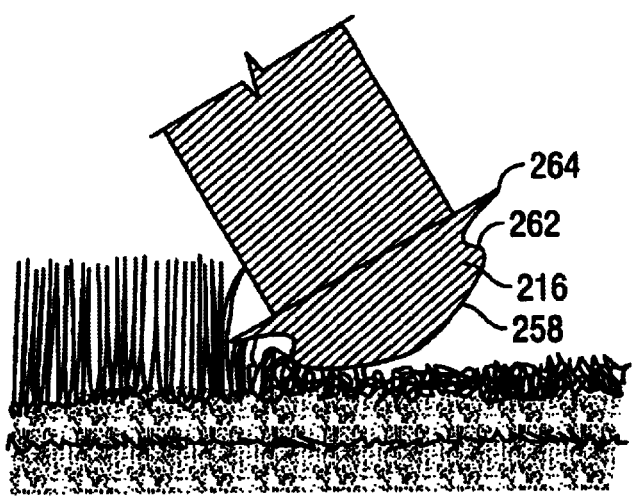
FIG. 7 is a side view illustrating another alternative embodiment of an electrode.
Figure 8:
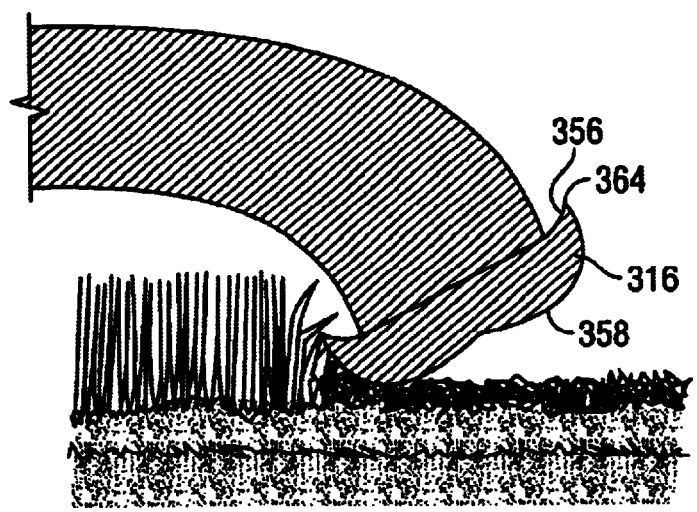
FIG. 8 is a side view illustrating a further alternative embodiment of an electrode.

FIGS. 6 to 8 illustrate alternative embodiments of electrodes. The electrode 116 of FIG. 6 has leading and trailing edges 164 that are sharper than in the embodiment hereinbefore described. It is believed that the sharper the edge, the higher temperature adjacent to the edge. The sharper edge may also be used for contacting or scraping of collagen fibrils. The electrode 216 of FIG. 7 is similar to the electrode 116 of FIG. 6 in that it has a sharp edge 264. In addition, the electrode 216 has a cam surface 262 to assist in keeping the leading edge 264 elevated. The electrode 216 of FIG. 7 also has a lower face 258 which is not entirely flat, but is more conical in shape to allow for more flexibility in use. In the embodiment of FIG. 8, an electrode 316 is provided which is similar in shape to the electrode 16 of FIG. 2. A conical step 356 is formed instead of a flat step, so that the leading edge 364 points away from a lower face 358 at a much larger angle than in the other embodiments hereinbefore described. Such a large angle further assists in keeping high temperature away from viable cartilage and possibly damaging the viable cartilage.

Figure 9:
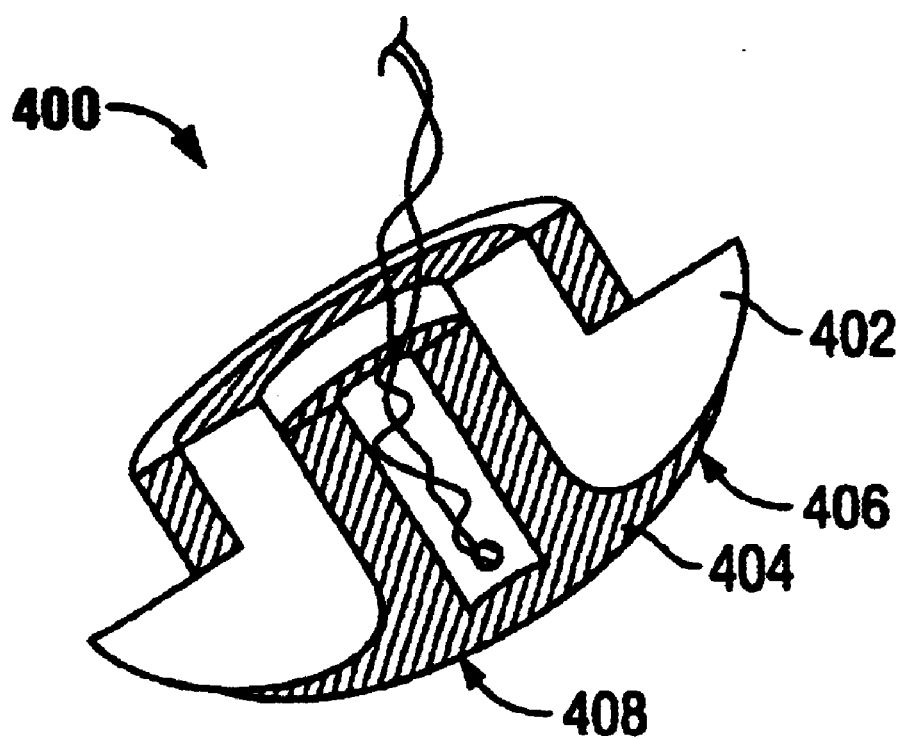
FIG. 9 is a perspective view of an electrode structure having an electrode and an electrically insulating material forming a face of the electrode structure, according to yet a further embodiment of the invention.

In all of the embodiments hereinbefore described, the electrode itself has a face which contacts the partially denatured fibrils, for example, the face 58 in FIG. 2. In another embodiment, the electrode may form only part of an electrode structure that otherwise has the features of, for example, the electrode 16 of FIG. 2. In FIG. 9, for example, an electrode structure 400 is formed by a combination of an electrode 402 and a thermally conductive and electrically insulating material 404. The electrode 402 has similar dimensions as the electrode 16 of FIG. 2. However, the material 404 is formed over a face 406 of the electrode. An outer surface 408 of the material 404 forms a face of the electrode structure 400. The surface 408 is used for contacting partially denature collagen fibrils.

In another embodiment, there may be more than one electrode. It may, for example, be possible to create a temperature profile such as in FIG. 3 with two electrodes. The two electrodes may be similar to one another, but be energized to different levels so that one electrode is warmer than the other.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. An electrosurgical instrument comprising:
   a holding formation;
   an elongated probe connected to and extending from the holding formation;
   an electrode on an end region of the elongated probe opposite the holding formation, the electrode including a protruding leading edge and a face, the electrode being locatable so that the face is substantially in a horizontal plane while the leading edge is above the horizontal plane; and
   a conductor extending along the elongated probe and having a portion connected to the electrode to provide RF power thereto, the electrode creating a temperature profile with a first temperature adjacent to the leading edge being higher than a second temperature adjacent to the face.

2. The electrosurgical instrument of claim 1, wherein the leading edge has a smaller radius of curvature than the face.

3. The electrosurgical instrument of claim 2, wherein the face is substantially flat.

4. The electrosurgical instrument of claim 2, wherein the leading edge is substantially sharp.

5. The electrosurgical instrument of claim 2, wherein the leading edge points in a direction away from the horizontal plane.

6. The electrosurgical instrument of claim 1, wherein there is no material of the electrode directly below the leading edge in the horizontal plane.

7. The electrosurgical instrument of claim 1, wherein the electrode has a convex cam surface between the leading edge and the face.

8. The electrosurgical instrument of claim 7, wherein the convex cam surface extends up to the leading edge.

9. The electrosurgical instrument of claim 1, wherein there is no material of the electrode below the leading edge in the horizontal plane, and the leading edge points in a direction away from the horizontal plane.

10. The electrosurgical instrument of claim 1, wherein the electrode has a trailing edge on a side of the face opposite the leading edge, the trailing edge being at substantially the same distance from the horizontal plane as the leading edge.

11. The electrosurgical instrument of claim 1, wherein the electrode has an electrode opening therein.

12. The electrosurgical instrument of claim 11, wherein the electrode opening has a diameter which is less than 50% of a diameter of the electrode measured in the same plane.

13. The electrosurgical instrument of claim 11, wherein the electrode opening extends through the face.

14. The electrosurgical instrument of claim 13, further comprising:
   a thermally conductive plug in the opening at or near the face; and
   a thermocouple in contact with the thermally conductive plug.

15. The electrosurgical instrument of claim 14, wherein the thermally conductive plug, at least at or near the face, is made of an electrically insulating material.

16. The electro surgical instrument of claim 1, further comprising a thermocouple located sufficiently close to the face to receive heat from the face.

17. The electrosurgical instrument of claim 1, wherein a line at right angles to the horizontal plane is at an angle with respect to an axis of the elongated probe.

18. The electrosurgical instrument of claim 17, wherein the angle is at least 30° C.

19. The electrosurgical instrument of claim 17, wherein a lower surface of the elongated probe is in a plane above the horizontal plane.

20. The electrosurgical instrument of claim 1, wherein the holding formation is a handle.

21. An electrosurgical instrument, comprising:
   a holding formation;
   an elongated probe connected to and extending from the holding formation;
   an electrode on an end region of the elongated probe opposite the holding formation, the electrode including a face in a horizontal plane and a protruding leading edge above the horizontal plane, with no material of the electrode below the leading edge in the horizontal plane; and
   a conductor extending along the elongated probe and being connected to the electrode to supply RF power to the leading edge and the face.

22. The electrosurgical instrument of claim 21, wherein movement of the electrode in a horizontal direction causes the leading edge to pass through a vertical plane before the face passes through the vertical plane.

23. The electrosurgical instrument of claim 22, wherein the leading edge has a smaller radius of curvature than the face.

24. The electrosurgical instrument of claim 23, wherein the leading edge points in a direction upward and to the left.

25. The electrosurgical instrument of claim 21, wherein the electrode has another edge on a side of the face different than the leading edge, the other edge being located above the horizontal plane with no material of the electrode below the other edge in the horizontal plane.

26. The electrosurgical instrument of claim 25, wherein the other edge is a trailing edge and the side is a trailing side of the face opposite the leading edge.

27. The electrosurgical instrument of claim 21, wherein a line at right angles to the horizontal plane is at an angle with respect to an axis of the elongated probe.

28. An electrosurgical instrument, comprising:
   a holding formation;
   an elongated probe connected to and extending from the holding formation, the elongated probe having an outer surface and a power conductor extending within the outer surface, the outer surface being at least partially electrically insulated from the power conductor; and
   an electrode on an end region of the elongated probe opposite the holding formation, the power conductor being electrically coupled to the electrode to provide RF power through the power conductor to the electrode, the holding formation being movable to insert the electrode through a surgical portal in a body of a person, followed by at least a portion of the elongated probe, the electrode including a protruding leading edge and a face, the holding formation being movable in a selected direction to progress the leading edge through degenerative collagen fibrils having bases attached to cartilage, the leading edge progressing through the fibrils at locations at a selected distance from the cartilage and creating a first temperature at or near the leading edge, further movement of the holding formation in the selected direction moving the face over the cartilage closer to the cartilage than the selected distance and creating a second temperature at or near the face, the second temperature being less than the first temperature.

29. The electrosurgical instrument of claim 28, wherein an insertion direction in which the electrode is inserted into the surgical portal in the same direction as the selected direction.

30. The electrosurgical instrument of claim 28, wherein the face is substantially planar and the protruding leading edge is locatable above a plane of the face.

31. A method of treating degenerative collagen fibrils having bases attached to viable cartilage, comprising:

locating a face of an electrode structure adjacent to the viable cartilage;

generating a temperature profile having a low temperature adjacent to the face and a high temperature at a location further from the viable cartilage than the face; and moving the electrode structure in a direction substantially parallel to a plane of the viable cartilage, such movement first exposing each fibril to the location of the temperature profile having the high temperature, whereafter the face moves over the fibril.

32. The method of claim 31, wherein the location on the temperature profile having the high temperature passes through an imaginary plane normal to the plane of the viable cartilage before the face passes through the imaginary plane.

33. The method of claim 31, wherein the electrode structure further includes a protruding leading edge corresponding to the location of the temperature profile having the high temperature, and moving the electrode structure comprises first exposing each fibril to the protruding leading edge.

34. The method of claim 33, wherein the face and the protruding leading edge are part of a single electrode, and moving the electrode structure comprises moving the single electrode.

35. An electrosurgical instrument comprising:

a holding formation;

an elongated probe connected to and extending from the holding formation;

an electrode on an end region of the elongated probe opposite the holding formation, the electrode including a leading edge and a face, the electrode being locatable so that the face is substantially in a horizontal plane while the leading edge is above the horizontal plane; and a conductor extending along the elongated probe and having a portion connected to the electrode to provide RF power thereto, the electrode creating a first temperature profile with a temperature adjacent to the leading edge being higher than a second temperature adjacent to the face, wherein the electrode has an electrode opening therein.

36. The electrosurgical instrument of claim 35, wherein the electrode opening has a diameter which is less than 50% of a diameter of the electrode measured in the same plane.

37. The electrosurgical instrument of claim 35, wherein the electrode opening extends through the face.

38. The electrosurgical instrument of claim 37, further comprising:

a thermally conductive plug in the opening at or near the face; and a thermocouple in contact with the thermally conductive plug.

39. The electrosurgical instrument of claim 38, wherein thermally conductive plug, at least at or near the face, is made of an electrically insulating material.

* * * * *